(12) United States Patent
Holland et al.

(10) Patent No.: US 9,669,203 B2
(45) Date of Patent: Jun. 6, 2017

(54) METHODS OF ENHANCING DELIVERY OF DRUGS USING ULTRASONIC WAVES AND SYSTEMS FOR PERFORMING THE SAME

(75) Inventors: Christy K. Holland, Cincinnati, OH (US); Kathryn E. Hitchcock, Cincinnati, OH (US); Kevin Haworth, Cincinnati, OH (US); Nikolas Ivancevich, Seattle, WA (US); T. Douglas Mast, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 1149 days.

(21) Appl. No.: 13/409,634

(22) Filed: Mar. 1, 2012

(65) Prior Publication Data
US 2012/0271167 A1  Oct. 25, 2012

Related U.S. Application Data

(60) Provisional application No. 61/447,867, filed on Mar. 1, 2011.

(51) Int. Cl.
*A61M 37/00* (2006.01)
*A61B 8/08* (2006.01)

(52) U.S. Cl.
CPC ....... *A61M 37/0092* (2013.01); *A61B 8/0833* (2013.01); *A61B 8/481* (2013.01)

(58) Field of Classification Search
CPC ... A61B 8/0833; A61B 8/481; A61M 37/0092
See application file for complete search history.

(56) References Cited

U.S. PATENT DOCUMENTS

| | | | |
|---|---|---|---|
| 6,575,922 B1 | 6/2003 | Fearnside et al. | |
| 2004/0265393 A1* | 12/2004 | Unger et al. | 424/600 |
| 2006/0264809 A1* | 11/2006 | Hansmann et al. | 604/22 |
| 2007/0161902 A1 | 7/2007 | Dan | |
| 2008/0319375 A1* | 12/2008 | Hardy | 604/22 |
| 2012/0130288 A1* | 5/2012 | Holland et al. | 601/2 |

FOREIGN PATENT DOCUMENTS

| | | |
|---|---|---|
| WO | WO2008062342 A2 | 5/2008 |
| WO | WO2008157422 A1 | 12/2008 |
| WO | WO2010108104 A1 | 9/2010 |

\* cited by examiner

*Primary Examiner* — Amanda Lauritzen Moher
(74) *Attorney, Agent, or Firm* — Dinsmore & Shohl LLP (57) ABSTRACT

Methods and systems for inducing and passively detecting stable cavitation and/or inertial cavitation for targeted drug delivery across a biological membrane are disclosed. Such methods include administering vesicles having a nucleating agent and a therapeutic drug to a vascular system of a patient, and providing an active interval of ultrasonic exposure substantially throughout a targeted treatment zone. The ultrasonic exposure is produced by a source transducer at a specified fundamental frequency, amplitude, duty cycle, and duration. The methods also include detecting a scattered ultrasonic wave, where the scattered ultrasonic wave is received by a detection transducer. Detection of the scattered ultrasonic wave is indicative of stable and/or inertial cavitation. The ultrasonic exposure is provided intermittently in the active intervals separated by rest periods, and substantially less ultrasonic exposure is provided during the rest period than during the active interval.

18 Claims, 7 Drawing Sheets

METHODS OF ENHANCING DELIVERY OF DRUGS USING ULTRASONIC WAVES AND SYSTEMS FOR PERFORMING THE SAME

This application claims priority to U.S. Provisional Application Ser. No. 61/447,867, filed Mar. 1, 2011, the content of which is hereby incorporated by reference in its entirety.

TECHNICAL FIELD

The present invention relates to methods and systems of inducing, detecting, and enhancing stable cavitation and/or inertial cavitation using ultrasonic waves. More specifically, the present invention relates to methods and systems of inducing, passively detecting, and enhancing stable cavitation and/or inertial cavitation during drug delivery across a biological membrane.

BACKGROUND

Providing efficient and safe methods for the delivery of drugs to target cells is a principal goal of a clinically useful pharmacotherapeutic strategy. In general, when a drug is administered systematically, only a small fraction of the drug may actually reach the target tissue. Thus, large system-wide total doses to achieve the effective local concentration of the drug in the target tissue may be required. Accordingly, systemic toxicity may be the dose limiting factor.

For atherosclerosis, an ideal targeted delivery agent could deliver large payloads of therapeutic drugs to the active atheroma, stabilizing the vulnerable area that is prone to rupture while minimizing systemic and non-specific drug effects. This would be a tool of critical importance for physicians in cases, such as, known carotid or coronary artery disease when direct, definite treatment could prevent the need for risky surgery.

Accordingly, methods and systems for ultrasound-enhanced delivery of drugs using stable cavitation and/or inertial cavitation are needed.

SUMMARY OF THE INVENTION

In one embodiment, a method for inducing and passively detecting stable cavitation for targeted drug delivery across a biological membrane includes administering vesicles that include a nucleating agent and a therapeutic drug to a vascular system of a patient, and providing an active interval of ultrasonic exposure substantially throughout a targeted treatment zone within the vascular system of the patient. The ultrasonic exposure is produced by a source transducer at a specified fundamental frequency, amplitude, duty cycle, and duration. The method also includes detecting a scattered ultrasonic wave, where the scattered ultrasonic wave is received by a detection transducer and the scattered ultrasonic wave includes a derivative frequency of the fundamental ultrasonic frequency comprising at least one of a subharmonic frequency and an ultraharmonic frequency. Detection of the derivative frequency is indicative of stable cavitation. The ultrasonic exposure is provided intermittently in the active intervals separated by rest periods, and substantially less ultrasonic exposure is provided during the rest period than during the active interval.

In another embodiment, a method for inducing and passively detecting inertial cavitation for targeted drug delivery across a biological membrane includes administering vesicles that include a nucleating agent and a therapeutic drug to a vascular system of a patient and providing an active interval of ultrasonic exposure substantially throughout a targeted treatment zone within the vascular system of the patient. The ultrasonic exposure is produced by a source transducer at a specified fundamental frequency, amplitude, duty cycle, and duration. The method also includes detecting a scattered ultrasonic wave, where the scattered ultrasonic wave is received by a detection transducer and the scattered ultrasonic wave includes inharmonic frequencies that are excited across a broadband spectrum, wherein detection of inharmonic scattered ultrasonic waves across the broadband spectrum is indicative of inertial cavitation. The ultrasonic exposure is provided intermittently in the active intervals separated by rest periods, and substantially less ultrasonic exposure is provided during the rest period than during the active interval.

In still another embodiment, a system for inducing and passively detecting cavitation during targeted drug delivery of vesicles comprising a nucleating agent and a therapeutic drug includes a source transducer electrically coupled to an ultrasonic driver. The ultrasonic driver is adapted to generate energy that can be converted at the source transducer to ultrasonic exposure suitable for inducing stable cavitation and/or inertial cavitation of the nucleating agent of the vesicles positioned proximate to a targeted treatment zone of a patient to increase absorption of the therapeutic drug in the targeted treatment zone. The system also includes a detection transducer electrically coupled to a digital computing device that detects scatter ultrasonic waves across a broadband spectrum and computes the presence of stable cavitation and/or inertial cavitation in the targeted treatment zone, wherein the system is adapted to intermittently provide a continuous wave of ultrasonic exposure at a ultrasonic exposure, wherein the source transducer provides an ultrasonic frequency substantially throughout the targeted treatment zone of the patient that is at a fundamental ultrasonic frequency, and the system receives scattered ultrasonic waves comprising frequencies that are indicative of the cavitation activity of the vesicles.

These and other features and advantages of these and other various embodiments according to the present invention will become more apparent in view of the drawings, detailed description, and claims provided herein.

BRIEF DESCRIPTION OF THE DRAWINGS

The following detailed description of the embodiments of the present invention can be better understood when read in conjunction with the following drawings, where like structure is indicated with like reference numerals, and in which.

Skilled artisans appreciate that elements in the figures are illustrated for simplicity and clarity and are not necessarily drawn to scale. For example, the dimensions of some of the elements in the figures may be exaggerated relative to other elements, as well as conventional parts removed, to help to improve understanding of the various embodiments of the present invention.

DETAILED DESCRIPTION OF THE INVENTION

The following terms are used in the present application:

In the context of stable cavitation, the terms "inducing" and "inducement" are used interchangeably herein to refer to the nucleation or initiation of stable cavitation and maintaining the persistence of stable cavitation temporally.

In the context of passively detecting stable cavitation, the term "passively" is used herein to refer to receiving a signal with a transducer or hydrophone which is used exclusively to receive emitted and/or scattered ultrasonic waves from acoustically activated bubbles. In the context of a system for inducing and passively detecting stable cavitation, the term "passive" is used herein to refer to a transducer and/or a hydrophone which is used exclusively to receive emitted and/or scattered ultrasonic waves from acoustically activated bubbles.

The term "cavitation" is used herein to refer to the formation, oscillation, and/or collapse of gaseous and/or vapor bubbles in a liquid due to an acoustic pressure field. Cavitation is generally classified into two types: stable cavitation and inertial cavitation. The term "stable cavitation" is used herein to refer to a microbubble or nanobubble oscillating in an ultrasound field, whereby the predominant acoustic emissions occur not only at the fundamental ultrasonic frequency and harmonic frequencies but also at the subharmonic and ultraharmonic frequencies. The origin of these emissions is a nonlinear standing wave, i.e. a Faraday wave, on the outer surface of the bubble, or nonlinear volumetric oscillations of the bubble during pulsation in the sound field. The term "inertial cavitation" is used herein to refer to cavitation which results in broadband emissions.

The term "drug delivery across the biological membrane" is used herein to refer to ultrasound-enhanced or ultrasound-mediated modification of the permeability of the cell membrane, which may include cells or membranes made of up cells. Drug delivery across the biological membrane employs the acoustic cavitation of microbubbles and/or nanobubbles to enhance delivery of molecules across the biological membrane for increased concentration of the drug as compared with a systemic dose and/or increased penetration as compared with an non-ultrasound-enhanced dosage.

The term "ultrasonic exposure" is used herein to refer to the ultrasound peak-to-peak pressure amplitude, duration, duty cycle, and quiescent period, or rest period, that is produced by a source transducer.

The term "targeted treatment zone" is used herein to refer to a diseased area of the patient that requires delivery of a therapeutic drug. In the case of a patient having atherosclerosis, the term "targeted treatment zone" is used herein to refer to the area of the vascular system of the patient having atheromatous plaques. In one embodiment, the targeted treatment zone may be positioned within a coronary artery of the patient. In another embodiment, the targeted treatment zone may be positioned within a carotid artery of the patient. In yet another embodiment, the targeted treatment zone may be positioned within a mammalian subject and refers to the area surrounding and comprising atheromatous plaques. In yet further embodiments, the targeted treatment zone may be positioned proximate to a cancerous tumor within the patient. In a specific embodiment, in the case of targeted drug delivery across a biological membrane in a targeted treatment zone, the term "targeted treatment zone" refers to the area encompassed by the −6 dB focal volume of the source transducer, which is confocally aligned with the −6 dB focal volume of the passive cavitation detector.

The term "source transducer" is used herein to refer to a transducer which produces an ultrasonic exposure. The term "detection transducer" is used herein to refer to a transducer which receives scattered ultrasonic waves.

The term "fundamental ultrasonic frequency", as used herein, refers to the frequency of ultrasonic exposure generated by a source transducer producing pressure cycles per unit time. The fundamental ultrasonic frequency employed herein can range from about 100-kHz to about 15-MHz, or from about 100 kHz to about 10-MHz. In one embodiment, the fundamental ultrasonic frequency is about 1-MHz.

When the fundamental ultrasonic frequency activates nano- or microbubbles, the bubbles scatter ultrasonic exposure at a derivative frequency. Thus, the term "scattered ultrasonic wave" is used herein to refer to the pressure amplitude or the intensity of the ultrasonic waves which are scattered from ultrasonically activated nano- and microbubbles.

The term "derivative frequency" is used herein to refer to any ultrasonic frequency or combination of ultrasonic frequencies scattered by bubbles undergoing stable cavitation. The derivative frequency is selected from a subharmonic frequency, an ultraharmonic frequency, and a plurality of ultraharmonic frequencies of the fundamental ultrasonic frequency applied to a treatment zone.

The term "harmonic frequency" is used herein to refer to integer multiples of the fundamental ultrasonic frequency. The term "subharmonic frequency" is used herein to refer to rational fractions of the fundamental ultrasonic frequency that are less than the fundamental frequency. The detection of scattered subharmonic frequencies is indicative of stable cavitation. The term "ultraharmonic frequency" is used herein to refer to integer multiples of the subharmonic frequency, excluding integer multiples of the fundamental frequency (i.e., for a fundamental frequency $F_0$, the ultraharmonic frequencies include $3F_0/2$, $5F_0/2$, $7F_0/2$, etc.). The detection of scattered ultraharmonic frequencies is also indicative of stable cavitation.

The term "inharmonic frequencies" is used herein to refer to broadband frequencies that do not contain the fundamental, harmonic, subharmonic, or ultraharmonic frequencies. The detection of scattered inharmonic frequencies is also indicative of inertial cavitation.

The term "dual-element annular transducer array" is used herein to refer to an array consisting of two transducer elements, wherein an annular element surrounds a central circular element. The term "single element transducer" is used herein to refer to a single element transducer that produces ultrasonic pressure waves. The term "linear array transducer" is used herein to refer to a multi-element transducer composed of a plurality of transducer elements. The transducer elements are electrically separate elements generally arranged along a line or curve. The term "two-dimensional array transducer" is used herein to refer to a matrix of transducer elements which provide beam control over a cross-sectional area. If the matrix is arranged in annuli, or concentric circles, the beam control provides spherical focusing at different depths from the face of the array. In the context of a transducer array, individual elements of the array may be square, hexagonal, annular, circular, or any other pattern which substantially or partially fills the emitting area of the transducer and can be controlled by a suitable driver system.

The term "focus or natural focus" is used herein to refer to the location of maximum pressure amplitude in the ultrasound field emitted by a source a transducer. The focus or natural focus employed herein can range from about 0.1 centimeters to about 30 centimeters, or from about 0.1 centimeters to 10 centimeters. As used herein, the terms "natural focus" and "focus" are interchangeable.

The term "hydrophone" is used herein to refer to a microphone configured to record and/or to listen to ultrasound scattered by acoustically active bubbles.

The term "ultrasonic driver" is used herein to refer to a device having a radio frequency signal source and a power amplifier. Impedance matching circuitry between the power amplifier and transducer may optionally be employed to increase the efficiency of an ultrasonic driver.

The term "signal" is used herein to refer an electronic signal converted to or from an ultrasonic pressure wave. The hydrophone or detection transducer converts a pressure wave into a voltage signal as a function of time. The term "gated signal" is used herein to refer to a detected signal that is truncated in time such that only certain signals of the scattered ultrasonic waves are detected, and such that certain signals of the scattered ultrasonic waves are disallowed. The signals of the scattered ultrasonic waves that are detected are those that are emitted from a scattering source at a particular distance from the detection transducer.

The term "pre-amplifier" is used herein to refer to a device which prepares an electronic signal for recording and/or processing. The pre-amplifier circuitry may or may not be housed as a separate component. In the context of amplifying a signal, the term "amplifying" is used herein to refer to increasing the amplitude of the signal.

The term "digital computing device" is used herein to refer to a device which converts measured voltages into digital information. Waveforms are sampled with an analog to digital converter that is, at minimum, two times the frequency of the highest frequency component of the observed signal. The samples are stored and accumulate until a sufficient amount are taken to describe the waveform. The signals are then reassembled for display. In the context of storing a signal, the term "storing" is used herein to refer to a data set that is stored in the local memory or remote storage of a digital computing device.

In the context of acquiring a signal, the term "acquiring" is used herein to refer to the process of sampling the voltage received by the detection transducer, hydrophone, or passive cavitation detector and converting the resulting samples into digital numeric values that can be manipulated by a computer. In the context of acquiring a signal with a computer, the term "data acquisition" is used herein to refer to the conversion of analog waveforms into digital values for processing on a computer.

The term "duty cycle" is used herein to refer to the pulse duration divided by the pulse repetition period. The duty cycle employed herein can range from about 0.01% to about 100%.

The term "bandwidth" is used herein to refer to the range of frequencies wherein the signal's Fourier transform has a power greater than a specified fraction of the maximum value. In a specific embodiment, the bandwidth is the frequency interval within which the power is above a quarter of the maximum value (i.e., the −6 dB bandwidth). In one embodiment, the detection transducer is configured to receive a bandwidth centered at one or more subharmonic and/or ultraharmonic frequencies of the fundamental frequency.

The term "ultrasonic pressure amplitude" is used herein to refer to the peak rarefactional pressure amplitude. In one embodiment, the ultrasonic pressure amplitude employed herein can range from about 0.01 MPa to about 3.0 MPa, or from about 0.01 MPa to about 1.0 MPa.

In the context of stable cavitation, the term "enhanced" is used herein to refer to an increase in the number of ultrasonically activated bubbles or to an increase in the duration of bubble activity. The term "ultrasonically activated bubbles" is used herein to refer to bubbles oscillating in shape and/or volume due to ultrasound exposure. In the context of drug delivery across a biological membrane, the term "enhanced" is used herein to refer to an increase in concentration of the therapeutic drug in the targeted treatment zone and/or the depth of penetration of the therapeutic drug into the targeted treatment zone, as compared to the concentration and/or depth of penetration of the therapeutic drug in the vascular system of the patient without ultrasonic drug delivery across the biological membrane.

The term "nucleating agent" is used herein to refer to an agent that initiates cavitation when exposed to ultrasound.

The term "therapeutic drug" is used herein to refer to a therapeutic agent, such as a pharmaceutical, used in treatment of a patient. In some embodiments, the therapeutic drug may reduce atheromatous plaques that have accumulated subendothelially in the vascular system of the patient. In other embodiments, the therapeutic drug may be a cancer drug introduced to a tumor of the patient.

The term "active interval" is used herein to refer to continuous wave or pulsed wave ultrasound produced by a source transducer. The source transducer provides an ultrasonic exposure in an active interval. The term "active interval duration" is used herein to refer to the period of time for which an ultrasonic exposure is provided. In one embodiment, the active interval duration employed herein can range from about 10 milliseconds to about 5 minutes, or from about 10 milliseconds to about 60 seconds.

The term "rest period" is used herein to refer to providing substantially no ultrasonic exposure. The term "rest period duration" is used herein to refer to the period of time for which substantially no ultrasonic exposure is provided. In one embodiment, the rest period duration employed herein can range from about 100 millisecond to about 5 minutes, or from about 1 second to about 20 seconds.

The term "continuous wave ultrasound" is used herein to refer to a technique in which a transducer continuously emits ultrasound, wherein the ultrasound is varied sinusoidally.

The term "pulsed wave ultrasound" is used herein to refer to a technique in which a transducer emits ultrasound in pulses or tone bursts.

In the context of enhancing stable cavitation, the term "adjusting the ultrasonic exposure" is used herein to refer to increasing or decreasing the peak-to-peak pressure output, the duty cycle, and/or the duration of the source transducer.

The term "passive cavitation detector" is used herein to refer to a transducer or a hydrophone which receives a scattered level of ultrasound from acoustically active bubbles. The term "transducer array" is used herein to refer to a transducer array which receives a scattered level of ultrasound from acoustically active bubbles. In one embodiment, the transducer array is a passive transducer array.

The term "nanobubble" is used herein to refer to bubbles on the size scale of nanometers. The term "microbubble" is used herein to refer to bubbles on the size scale of micrometers.

The term "ultrasound contrast agent" is used herein to refer to gas-filled vesicles (containing nanobubbles or microbubbles), which are administered, for example, intravenously to the systemic circulation to increase echogenicity on an ultrasound image.

The term "protective material" is used herein to refer to a protein, lipid or surface active agent that prevents dissolution of an entrapped bubble.

The term "liposome" is used herein to refer to microscopic vesicle consisting of a core enclosed by one or more phospholipid layers, wherein hydrophobic compounds and/or hydrophilic compounds can be contained within the core. The term "echogenic liposome" is used herein to refer to a liposome which produces an echo when exposed to ultrasound.

The term "beamwidth" is used herein to refer to the spatial extent of the ultrasound beam at the focus or natural focus of a transducer. In one embodiment, the beamwidth is about −6 dB, such that the pressure output is at least a quarter of the peak value (−6 dB beamwidth). The "beamwidth" can be controlled by changing the diameter, aperture, or focusing of the transducer while keeping the frequency fixed. The beamwidth employed herein can range, for example, from about 0.1 centimeters to about 10 centimeters.

Embodiments of the present invention relate to ultrasound-mediated methods and systems of detecting and enhancing stable cavitation for targeted drug delivery of vesicles having a nucleating agent and a therapeutic drug. In one embodiment, a system for inducing and passively detecting stable cavitation and/or inertial cavitation is provided, the system comprising a source transducer electrically coupled to an ultrasonic driver, where the ultrasonic driver is adapted to generate energy that can be converted at the source transducer to an ultrasonic exposure suitable for inducing stable cavitation and/or inertial cavitation of a nucleating agent of the vehicles positioned proximate to the targeted treatment zone of the patient. The system also includes a detection transducer electrically coupled to a digital computing device that detects scattered ultrasonic waves across a broadband spectrum and computes the presence of stable cavitation and/or inertial cavitation in the targeted treatment zone. The system is adapted to intermittently provide a continuous wave or pulsed of ultrasonic exposure at an ultrasonic exposure substantially throughout the targeted treatment zone of the patient at a fundamental ultrasonic frequency and to receive scattered ultrasonic waves having frequencies that are indicative of the activity of the vesicles.

Figure 1:
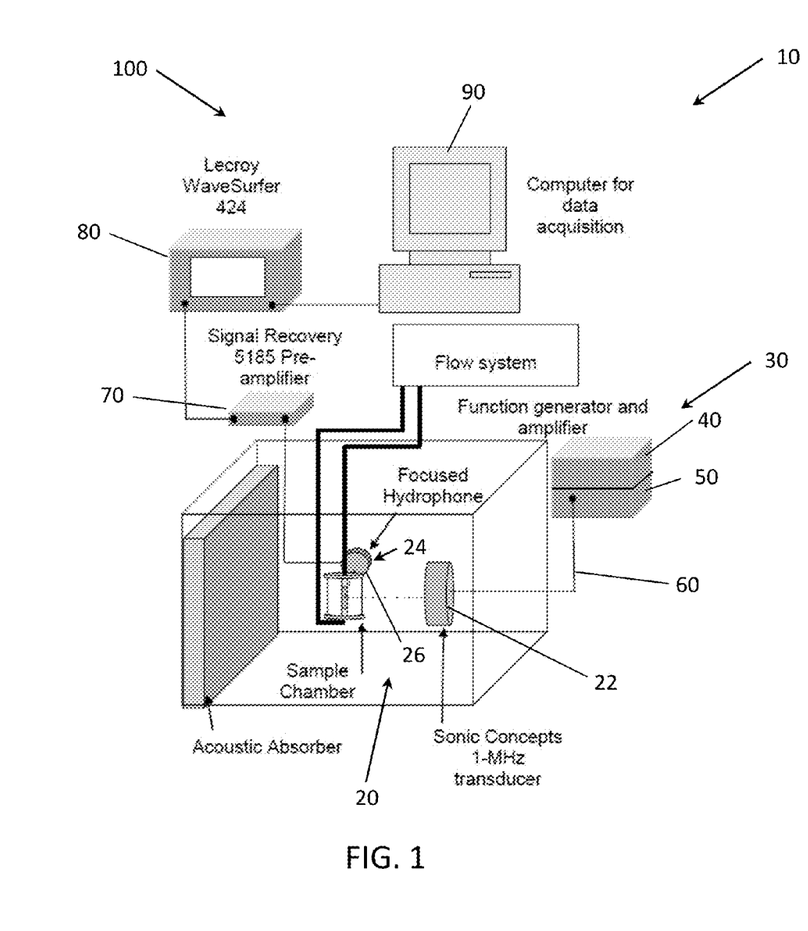
FIG. 1 is a schematic of a system for inducing and passively detecting stable cavitation and/or inertial cavitation during ultrasound-enhanced drug delivery experiments according to one or more embodiments shown and described herein.

As shown in FIG. 1, the system 10 for inducing and passively detecting stable cavitation and/or inertial cavitation is adapted to provide an ultrasonic exposure substantially throughout the targeted treatment zone of a patient and to receive scattered ultrasonic waves. The embodiment depicted in FIG. 1 is suited for laboratory investigation of ex vivo samples, however, could be adapted for in vivo treatment of patients. In one embodiment, the system 10 includes a source transducer 22 and a detection transducer 24. The source transducer 22 provides an ultrasonic exposure and the detection transducer 24 receives scattered ultrasonic waves, such that drug delivery across the biological membrane and stable cavitation and/or inertial cavitation detection may be achieved substantially simultaneously. The size and configuration of the source transducer 22 and the detection transducer 24 should be selected so that ultrasonic waves, or energy, may be provided substantially throughout the targeted treatment zone of a patient, while avoiding potentially harmful bioeffects such as tissue damage, petechial hemorrhage, blood brain barrier disruption, thermal coagulation, and/or cellular damage to the patient.

Figure 2:
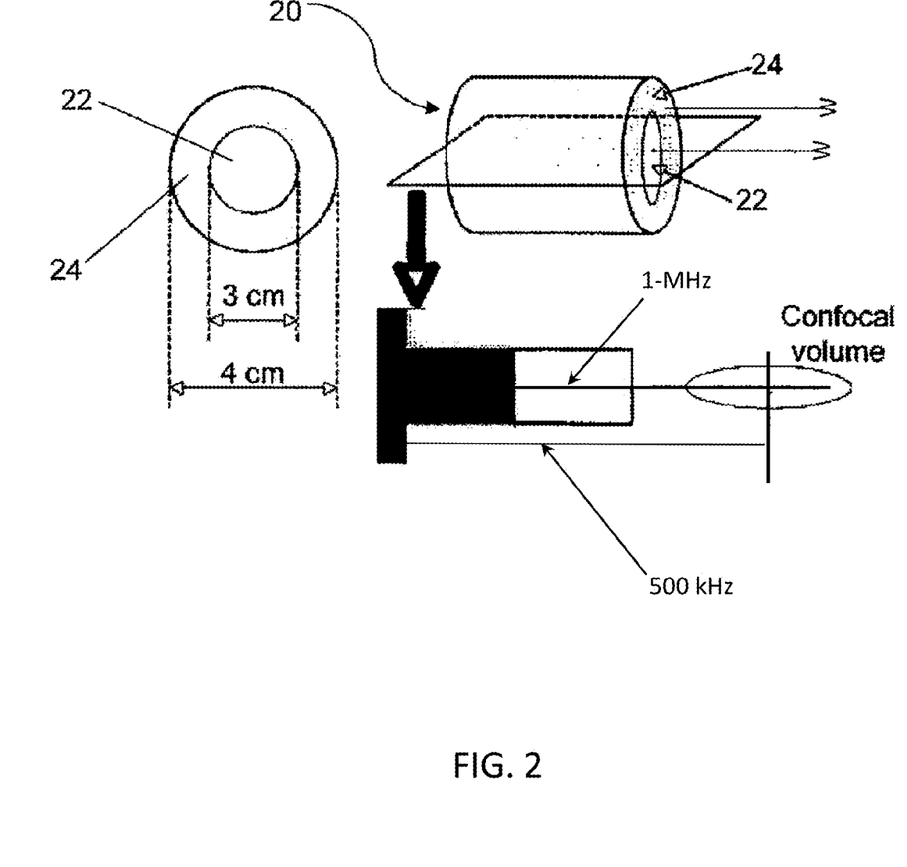
FIG. 2 is a schematic of a dual-element annular array comprising a 1-MHz ultrasound source and 500-kHz passive cavitation detector according to one or more embodiments shown and described herein.

In one embodiment, the source transducer 22 and the detection transducer 24 may be integrated into a dual-element annular transducer array 20, as depicted in FIG. 2. In this embodiment, the source transducer 22 has a circular cross-section having a diameter of about 3 centimeters, and the detection transducer 24 has an annular cross-section having an inner diameter of about 3 centimeters and an outer diameter of about 4 centimeters. In another embodiment, the detection transducer 24 has a circular cross-section having a diameter of about 3 centimeters, and the source transducer 22 has an annular cross-section having an inner diameter of about 3 centimeters and an outer diameter of about 4 centimeters. However, the dual-element annular transducer array 20 should not be limited to the particular aspects disclosed herein, but may comprise any configuration wherein a source transducer 22 is confocally aligned with a detection transducer 24. Moreover, the source transducer 22 may include the annular transducer element surrounding the central circular transducer element, or may include the central circular transducer element. Similarly, the detection transducer 24 may include the annular transducer element surrounding the central circular transducer element, or may include the central circular transducer element.

As discussed above, the source transducer 22 is adapted to provide an ultrasonic exposure. The source transducer 22 provides an ultrasonic frequency that is a fundamental ultrasonic frequency. Suitable fundamental frequencies produced by the source transducer 22 can range from about 100-kHz to about 15-MHz. In one embodiment, the source transducer 22 can produce a fundamental ultrasonic frequency from about 500-kHz to about 2-MHz. In another embodiment, the source transducer 22 can produce a fundamental ultrasonic frequency of about 1-MHz.

The source transducer 22 is configured such that it is adjustable to vary the duty cycle of the ultrasonic exposure produced. In one embodiment, the source transducer 22 is adjustable to vary the duty cycle from about 0.01% to about 100%. Moreover, the source transducer 22 can be configured such that it is adjustable to vary the beamwidth of the ultrasonic exposure produced. The beamwidth may be varied such that the source transducer 22 provides an ultrasonic exposure substantially throughout the targeted treatment zone of a patient. In one embodiment, the source transducer 22 is configured to provide a beamwidth of about 0.1 centimeters to about 10 centimeters. Additionally, the source transducer 22 may be configured such that it is adjustable to select an ultrasonic pressure amplitude of the ultrasonic exposure that is produced. In one embodiment, the source transducer 22 is configured to provide an ultrasonic pressure amplitude from about 0.01 MPa to about 3.0 MPa. In other embodiments, the source transducer 22 is configured to provide an ultrasonic pressure amplitude from about 0.1 MPa to about 1.0 MPa.

The detection transducer 24 is adapted to receive scattered ultrasonic waves substantially throughout the targeted treatment zone of a patient. The frequencies of the scattered ultrasonic waves are indicative of the behavior of the vesicles in the vascular system of the patient. In one embodiment, the detection transducer 24 receives an ultrasonic frequency that is a derivative frequency of the fundamental ultrasonic frequency selected from the group consisting of a subharmonic frequency, an ultraharmonic frequency, a plurality of ultraharmonic frequencies, and combinations thereof. In this embodiment, the detection transducer 24 is configured to receive a bandwidth centered at one or more subharmonic frequency and/or ultraharmonic frequency of the fundamental frequency. In yet another embodiment, the detection transducer 24 is configured to receive a bandwidth centered at the subharmonic frequency of about 500-kHz. In yet another embodiment, the detection transducer 24 is configured to receive a bandwidth centered at a frequency greater than five times the fundamental ultrasonic frequency. In certain embodiments, the detection transducer 24 is configured to receive a bandwidth centered at a frequency greater than an order of magnitude greater than the fundamental ultrasonic frequency Detection of a derivative frequency selected from the group consisting of a subharmonic frequency, an ultraharmonic frequency, a plurality of ultraharmonic frequencies, and combinations thereof, is indicative of stable cavitation during drug delivery across the biological membrane. The scattering of incident wave by ultrasonically activated bubbles on the size scale of nanometers or micrometers occurs at the center frequency and harmonics of the insonifying pulse. However, the presence of half of the fundamental frequency (the subharmonic) and its odd multiples (ultraharmonics) indicate the presence of microbubbles or nanobubbles that are cavitating stably.

Detection of scattered ultrasonic waves that are excited at broadband frequencies (i.e., inharmonic frequencies that are not concentrated at the subharmonic frequency and/or the ultraharmonic frequencies, nor the fundamental or harmonic frequencies) is indicative of inertial cavitation during drug delivery across the biological membrane. The scattered ultrasonic waves generally occur at all frequencies. Detection of inertial cavitation during drug delivery across the biological membrane may be improved by evaluating scattered ultrasonic waves at frequencies larger than the fundamental frequency, for example, by evaluating scattered ultrasonic waves at a frequency an order of magnitude greater than the fundamental ultrasonic frequency. Evaluation of scattered ultrasonic waves at these frequencies may decrease noise in the signal caused by the fundamental ultrasonic frequency.

Referring again to FIG. 1, the ultrasonic driver 30 is adapted to generate electrical energy that can be converted at the source transducer 22 to ultrasonic exposure suitable for penetrating a targeted treatment zone of a patient. In one aspect, the ultrasonic driver 30 includes a function generator 40, an amplifier 50, and a matching network 60. The ultrasonic driver 30 is electrically connected to the source transducer 22, such that the system 10 is adapted to provide an ultrasonic exposure substantially throughout the treatment zone of a patient. The ultrasonic driver 30 may be of a conventional design with an adjustable frequency generator and/or an adjustable power amplifier. The ultrasonic driver 30 should be configured such that the ultrasonic waves or energy can be selected to provide an ultrasonic exposure substantially throughout the treatment zone of a patient.

The function generator 40 is electrically connected to the amplifier 50. The amplifier 50 amplifies the electrical energy generated by the function generator 40. A matching network 60 may be electrically connected to the amplifier 50. The matching network 60 increases the efficiency of the ultrasonic driver 30 by impedance matching circuitry between the amplifier 50 and the source transducer 22. In this particular aspect, the matching network 60 is electrically connected to the source transducer 22.

The detection transducer 24 converts the scattered ultrasonic waves received into an electronic signal. In this embodiment, the derivative frequency received by the detection transducer 24 comprises a signal. In some embodiments, the signal received by the detection transducer 24 is gated. The signal is filtered such that the detection transducer 24 receives ultrasonic frequencies that are substantially a derivative frequency of the fundamental ultrasonic frequency. In one embodiment, the derivative frequency of the fundamental frequency received by the detection transducer 24 is selected from the group consisting of a subharmonic frequency, an ultraharmonic frequency, a plurality of ultraharmonic frequencies, and combinations thereof. Detection of such derivative frequencies is indicative of stable cavitation. In another embodiment, the detection transducer 24 receives a scattered ultrasonic wave that includes inharmonic frequencies that are excited across a broadband spectrum. Detection of such inharmonic frequencies is indicative of inertial cavitation.

The system 10 may further include a pre-amplifier 70. The pre-amplifier 70 is electrically connected to the detection transducer 24. The pre-amplifier 70 amplifies the signal received by the detection transducer 24.

The system 10 may include a digital computing device 100. The digital computing device may include a digital oscilloscope 80 and/or a computer 90. The digital oscilloscope 80 is electrically connected to the pre-amplifier 70. The digital oscilloscope 80 stores the signal amplified by the pre-amplifier 70. The computer 90 is electrically connected to the digital oscilloscope 80. The computer 90 acquires the signal stored in the digital oscilloscope 80. The computer 90 provides data acquisition from the signal stored in the digital oscilloscope 80.

The digital computing device 100 includes a processor and a memory electronically coupled to one another. A computer readable instruction set is stored in the memory of the digital computing device 100 and is executable by the processor of the digital computing device 100.

The system 10 may further include a hydrophone 26. The hydrophone 26 is adapted to receive scattered ultrasonic waves substantially throughout the targeted treatment zone of a patient. The hydrophone 26 converts the scattered ultrasonic waves received into an electronic signal. The derivative frequency received by the hydrophone 26 comprises a signal. In some embodiments, the signal received by the hydrophone 26 is gated, such that the hydrophone 26 receives scattered ultrasonic waves that are truncated to receive only signals from a selected location.

In another embodiment of the present invention, a method for inducing and passively detecting stable cavitation for targeted drug delivery is provided. The method includes administering vesicles including a nucleating agent and a therapeutic drug to a vascular system of a patient, and providing an active interval of ultrasonic exposure substantially throughout a targeted treatment zone within the vascular system of the patient, where the ultrasonic exposure is produced by a source transducer 22 at a specified fundamental frequency, amplitude, duty cycle, and duration. The method further includes detecting a scattered ultrasonic wave, where the scattered ultrasonic wave is received by a detection transducer 24. The scattered ultrasonic wave includes a derivative frequency of the fundamental ultrasonic frequency including at least one of a subharmonic frequency and an ultraharmonic frequency. Detection of the derivative frequency is indicative of stable cavitation. The ultrasonic exposure is provided intermittently in the active intervals which are separated by rest periods, and substantially less ultrasonic exposure is provided during the rest period than during the active interval.

The method for inducing and passively detecting stable cavitation may increase permeability of an endothelium of the patient to passage of the therapeutic drug across the endothelium. Thus, drug delivery across the biological membrane according to the methods described herein may increase concentration of the therapeutic drug in the targeted treatment zone of the patient.

The source transducer 22 and the detection transducer 24 used in the method for inducing and passively detecting stable cavitation may be selected from the group including at least two separate transducers, an annular transducer array, a linear transducer array, and a two-dimensional transducer array. In some embodiments, the scattered ultrasonic waves are detected by the detection transducer 24 that is a passive cavitation detector selected from the group including a hydrophone 26 and a transducer array.

As discussed above, the ultrasonic exposure is produced by a source transducer 22 at a fundamental ultrasonic frequency. Suitable fundamental frequencies produced by the source transducer 22 may be, for example, from about 100-kHz to about 15-MHz. In one embodiment, the source transducer 22 can produce a fundamental ultrasonic frequency from about 100-kHz to about 1-MHz. In another embodiment, the source transducer 22 may produce a fundamental ultrasonic frequency of about 500-kHz.

In another aspect, the source transducer 22 is configured such that it is adjustable to vary the focus or natural focus to assist in concentrating or directing ultrasonic waves or energy to the targeted treatment zone so that ultrasonic waves or energy may be provided substantially throughout the targeted treatment zone of a patient. In one particular aspect, the ultrasonic exposure is emitted from the source transducer 22 with a focus or natural focus from about 0.1 centimeters to about 30 centimeters. In a further aspect, the ultrasonic exposure is emitted from the source transducer 22 with a focus or natural focus from about 0.1 centimeters to about 10 centimeters. Moreover, the source transducer 22 is configured such that it is adjustable to vary the beamwidth of the ultrasonic exposure produced. The beamwidth may be varied such that the source transducer 22 provides an ultrasonic exposure substantially throughout the targeted treatment zone of a patient. In one aspect, the source transducer 22 is configured to provide a beamwidth of about 0.1 centimeter to about 10 centimeters.

The method also comprises detecting scattered ultrasonic waves, wherein the scattered ultrasonic waves are received by a detection transducer 24. The scattered ultrasonic waves are received by the detection transducer 24 and include a derivative frequency of the fundamental ultrasonic frequency selected from the group consisting of a subharmonic frequency, an ultraharmonic frequency, a plurality of ultraharmonic frequencies, and combination thereof. The component waves measured in the derivative frequency can be isolated by the digital oscilloscope 80, for example by implementing a spectrum analysis. In one specific aspect, the detection transducer 24 detects a subharmonic frequency of about 250-kHz for a fundamental ultrasonic frequency of about 500-kHz. As previously discussed, detecting a derivative frequency selected from the group consisting of a subharmonic frequency, an ultraharmonic frequency, a plurality of ultraharmonic frequencies, and combinations thereof, is indicative of stable cavitation during drug delivery across the biological membrane as the presence of half of the fundamental frequency (the subharmonic) and its odd multiples (ultraharmonics) indicate the presence of microbubbles and/or nanobubbles that are cavitating stably.

In yet another embodiment, a method for inducing and passively detecting inertial cavitation for targeted drug delivery is provided. The method includes administering vesicles including a nucleating agent and a therapeutic drug to a vascular system of a patient, and providing an active interval of ultrasonic exposure substantially throughout a targeted treatment zone within the vascular system of the patient, where the ultrasonic exposure is produced by a source transducer 22 at a specified fundamental frequency, amplitude, duty cycle, and duration. The method further includes detecting a scattered ultrasonic wave, where the scattered ultrasonic wave is received by a detection transducer 24. The scattered ultrasonic wave includes an inharmonic frequency in a broadband spectrum. Detection of the inharmonic frequency excited in the broadband spectrum is indicative of inertial cavitation. The ultrasonic exposure is provided intermittently in the active intervals which are separated by rest periods, and substantially less ultrasonic exposure is provided during the rest period than during the active interval.

The vesicles used in the methods described above include nucleating agents. Such nucleating agents may be selected from the group including nanobubbles, microbubbles, and ultrasound contrast agents. In one embodiment, the ultrasound contrast agent is perflutren-lipid microspheres, or Definity® (Lantheus Medical Imaging, N. Billerica, Mass.). The vesicles themselves include protective materials that encapsulate the nucleating agent and the therapeutic drug. Suitable protective materials include, but are not limited to, lipids and/or liposomes. Liposomes can entrap microbubbles, nanobubbles, and/or ultrasound contrast agents, enabling enhanced echogenicity and cavitation nucleation. In one particular aspect, the liposome is an echogenic liposome ("ELIP"). Transmission of each of the vesicles across the biological membranes of the targeted treatment zone may be enhanced at particular ultrasonic frequencies, amplitudes, durations, and duty cycles. Accordingly, each of the vesicles delivered to the targeted treatment zone may have an ultrasonic exposure that increases concentration of the therapeutic drug in the targeted treatment zone and/or the depth of penetration of the therapeutic drug into the targeted treatment zone. The ultrasonic frequencies, amplitudes, durations, and duty cycles of the ultrasonic exposures may be determined experimentally and provided to end-users for use in treating patients. Thus, the properties of the ultrasonic exposure are predetermined to induce stable cavitation and/or inertial cavitation in the vesicles.

In another embodiment, the digital computing device 100 may control the source transducer 22 to vary the ultrasonic frequencies, amplitudes, durations, and duty cycles produced to induce stable cavitation and/or inertial cavitation. The digital computing device 100 is connected to the source transducer 22 and the detection transducer 24 such that the digital computing device 100 forms a control feedback loop. The digital computing device 100 monitors the detection transducer 24 to determine if the intensity and duration of stable cavitation and/or inertial cavitation is occurring in the targeted treatment zone of the patient. The digital computing device 100 can vary the control parameters of the source transducer 22 to adjust the ultrasonic frequency, amplitude, duration, and duty cycle of the ultrasonic exposure produced by the source transducer 22. For example, the intensity of the stable cavitation and/or inertial cavitation in the targeted treatment zone of the patient may decrease over time, as the nucleating agents in the vesicles are consumed. Accordingly, when the digital computing device 100 determines that stable cavitation and/or inertial cavitation have fallen below a threshold limit, the digital computing device 100 terminates the active interval of the ultrasonic exposure and initiates a rest period, thereby allowing additional vesicles having nucleating agents to flow into the targeted treatment zone of the patient.

Echogenic liposomes can be targeted to certain tissues by attaching specific peptides, ligands, or antibodies to the surface of the liposome. Additionally, echogenic liposomes may be fragmented with ultrasound near a target tissue. In one specific aspect, echogenic liposomes can be targeted with peptides or ligands to bind to receptors characteristic of intravascular diseases (or blood clots). Targeting echogenic liposomes enables selective accumulation of the nucleating agent to a specific area. In one particular aspect, echogenic liposomes are targeted to a targeted treatment area comprising atheromatous plaques that have accumulated subendothelially within the vascular system of the patient.

The method of enhancing stable cavitation and/or inertial cavitation also includes administering a therapeutic drug to a targeted treatment zone of a patient. Without limitation, the therapeutic drug may be a medication, such as an anti-inflammatory drug (Rosiglitazone) or an anti-angiogenic drug (Bevicizumab), or a vasoconstrictor, or a bioactive gas, such as a vasodilator (nitric oxide), or neuroprotectants (Xenon).

The methods of enhancing stable cavitation and inertial cavitation also include providing an ultrasonic exposure substantially throughout the targeted treatment zone of a patient. The ultrasonic exposure is produced by a source transducer 22 and comprises a fundamental ultrasonic frequency. In one embodiment, the source transducer 22 may be a single element transducer, a linear array transducer, or a two-dimensional array transducer. In another embodiment, the source transducer 22 may be one element of a dual-element annular transducer array 20 having a circular cross-section having a diameter of about 3 centimeters.

Figure 3:
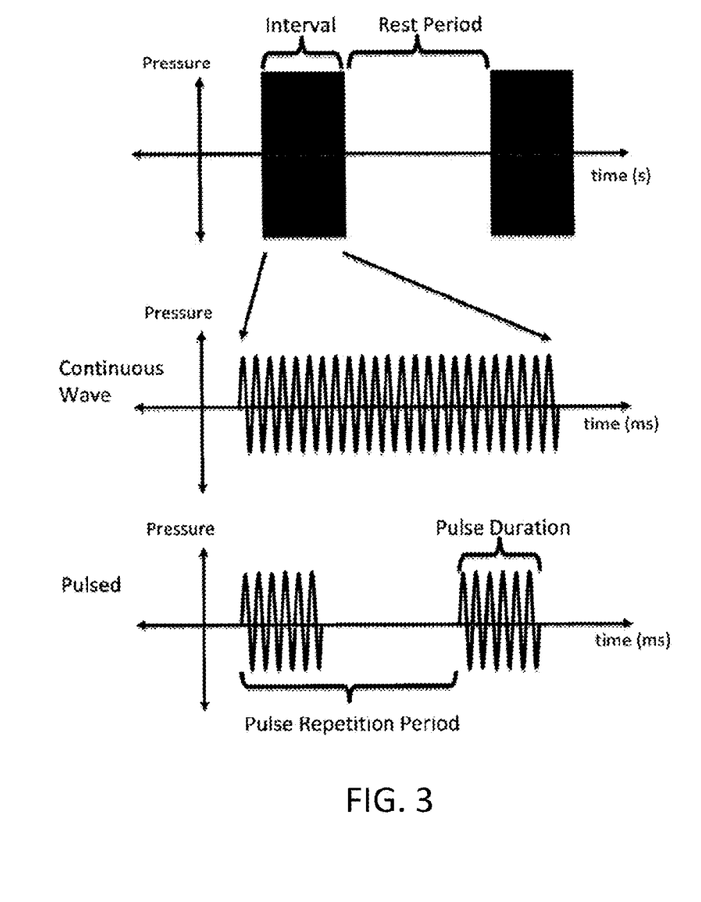
FIG. 3 is a schematic of the ultrasonic exposure being provided in active intervals separated by rest periods, wherein substantially less ultrasonic exposure is provided during the rest periods as compared to the active intervals according to one or more embodiments shown and described herein.

In yet another aspect, the source transducer 22 is configured such that it is adjustable to vary the focus or natural focus to assist in concentrating or directing ultrasonic waves or energy to the targeted treatment zone so that ultrasonic waves or energy may be provided substantially throughout the targeted treatment zone of a patient. In a further aspect, the ultrasonic exposure may be emitted from the source transducer 22 with a focus or natural focus from about 0.1 cm to about 30 cm. In still a further aspect, the ultrasonic exposure may be emitted from the source transducer 22 with a focus or natural focus from about 0.1 cm to about 10 cm. As shown in FIG. 3, the ultrasonic exposure produced by a source transducer 22 is provided in active intervals separated by rest periods, wherein substantially less ultrasonic exposure is provided during the rest periods. The active interval comprises either continuous wave or pulsed wave ultrasound produced by the source transducer 22; the rest period comprises a quiescent period. The active interval duration is dictated by the duration of stable cavitation and/or inertial cavitation and the rest period duration is dictated by the in-flow of the nucleating agent or ultrasound contrast agent.

The ultrasonic exposure is provided in active intervals to enhance stable cavitation and/or inertial cavitation. By providing an ultrasonic exposure in active intervals separated by rest periods, the nucleating agent is enabled to flow into the targeted treatment zone of the patient. The bubble activity that elicits stable cavitation and/or inertial cavitation, may be sustained using an intermittent or continuous infusion of a commercial contrast agent. Thus, providing an ultrasonic exposure in active intervals separated by rest periods allows vesicles including the nucleating agent to flow into the targeted treatment zone of the patient and enhances stable cavitation and/or inertial cavitation.

In one embodiment, the ultrasonic exposure is provided for an active interval duration from about 10 milliseconds to about 5 minutes. In a further aspect, the ultrasonic exposure is provided for an active interval duration from about 10 milliseconds to about 10 seconds. In still a further aspect, the ultrasonic exposure is provided for an active interval duration of about 8.5 seconds. In yet another aspect of this embodiment, the rest period duration is from about 100 milliseconds to about 5 minutes. In a further aspect, the rest period duration is from about 1 second to about 60 seconds. In another embodiment, the rest period duration is from about 1 second to about 30 seconds.

The source transducer 22 provides an ultrasonic exposure substantially throughout the targeted treatment zone of a patient, wherein the ultrasonic exposure is produced by a source transducer 22 and comprises a fundamental ultrasonic frequency. The ultrasonic exposure may comprise pulsed wave or continuous wave ultrasound. Suitable fundamental frequencies produced by the source transducer 22 include frequencies from about 100-kHz to about 15-MHz. In one embodiment, the source transducer 22 produces a fundamental ultrasonic frequency from about 500-kHz to about 3-MHz. In another embodiment, the targeted treatment zone comprises a clot and the source transducer 22 produces a fundamental ultrasonic frequency of about 1-MHz.

Figure 4:
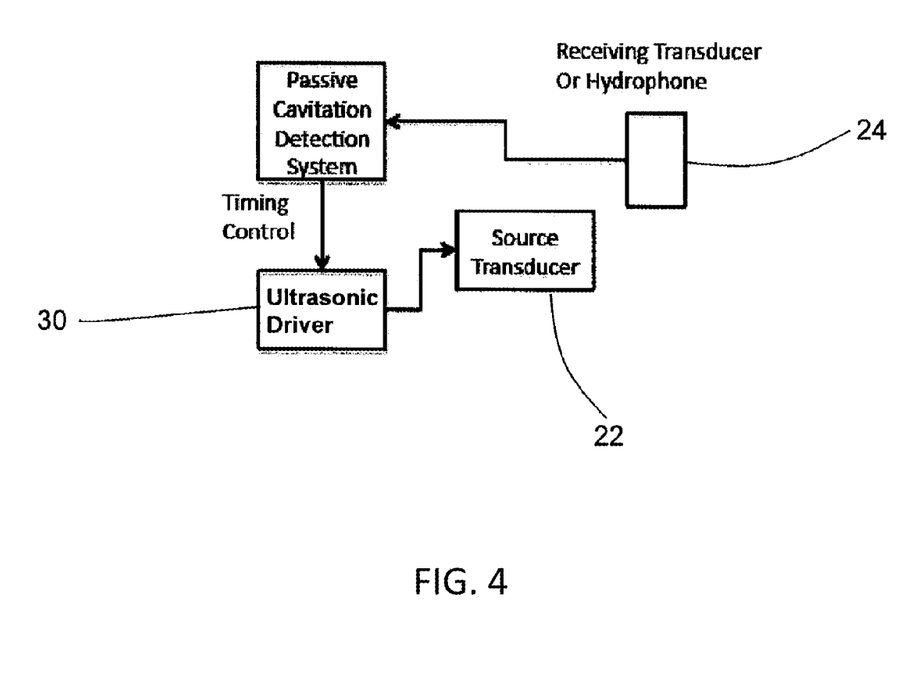
FIG. 4 is a block diagram of a passive stable cavitation detection and control system for ultrasound-enhanced drug delivery across a biological membrane according to one or more embodiments shown and described herein.

As shown in FIG. 4, the method of enhancing stable cavitation further includes detecting scattered ultrasonic waves. The scattered ultrasonic waves are received by a detection transducer 24. The scattered ultrasonic waves include a derivative frequency of the fundamental frequency selected from the group consisting of a subharmonic frequency, an ultraharmonic frequency, a plurality of ultraharmonic frequencies, and combinations thereof. In one embodiment, the scattered ultrasonic waves are received by a passive cavitation detector. In a further embodiment, the detection transducer 24 is a passive cavitation detector that is selected from the group consisting of a hydrophone 26 and a passive transducer array.

Similarly, the method of enhancing inertial cavitation further includes detecting scattered ultrasonic waves by a detection transducer 24. The scattered ultrasonic waves include inharmonic frequencies that are excited across a broadband spectrum. Detection of scattered inharmonic ultrasonic waves across the broadband spectrum is indicative of inertial cavitation. In one embodiment, the scattered ultrasonic waves are received by a passive cavitation detector. In a further embodiment, the detection transducer 24 is a passive cavitation detector that is selected from the group consisting of a hydrophone 26 and a passive transducer array.

Figure 5:
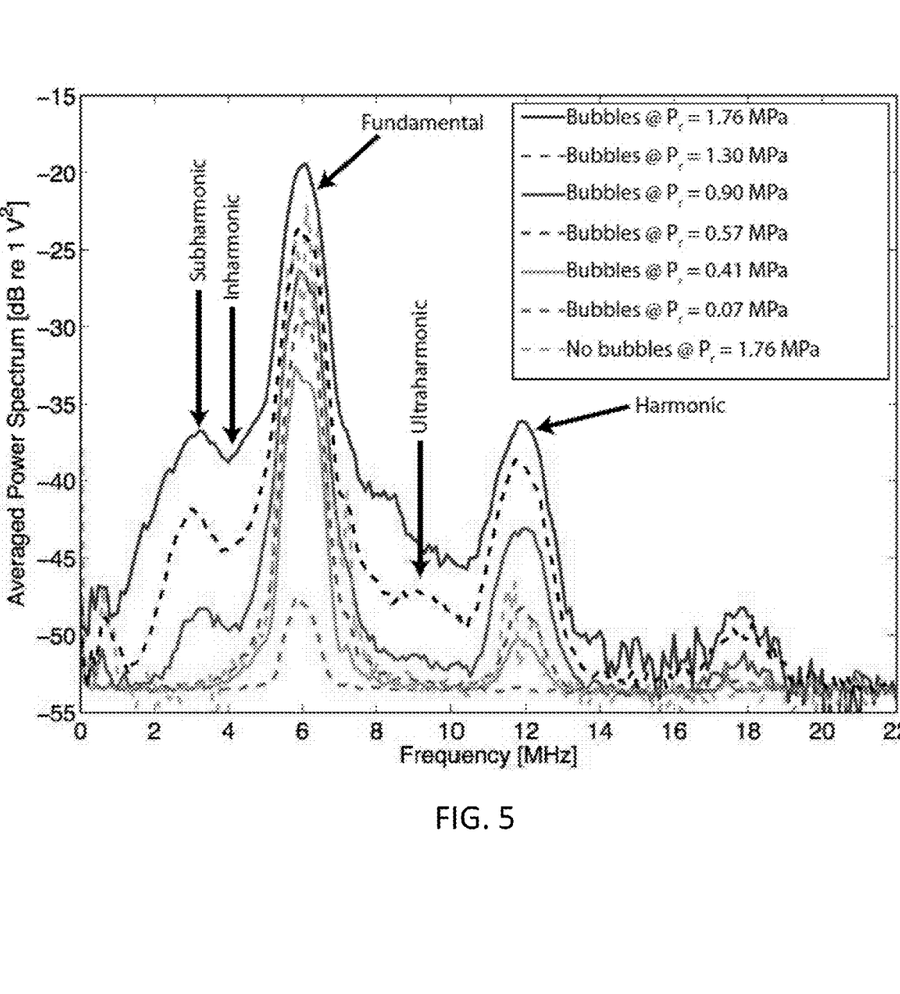
FIG. 5 is a graph depicting the representative frequency spectrum traces used for stable cavitation and inertial cavitation detection caused by exposure to ultrasonic waves according to one or more embodiments shown and described herein.

Depictions of frequency spectrum traces from a signal analyzer that is used to detect cavitation are shown in FIG. 5, measuring cavitation caused by exposure of echogenic liposomes in an in vitro flow model to 6-MHz pulsed ultrasound. The exposure peak rarefactional pressure amplitudes ranged from 0.07 MPa to 1.76 MPa. Stable and inertial cavitation were detected at peak rarefactional pressure amplitudes from 0.90 to 1.76 MPa. Note the 3-MHz peak on these traces corresponding to the subharmonic emissions indicative of stable cavitation. Inharmonic emissions are also evident at 4, 8, and 10-MHz on these traces and are indicative of inertial cavitation.

In some embodiments, the methods of enhancing stable cavitation and/or inertial cavitation further include adjusting the ultrasonic exposure produced by the source transducer 22 in accordance with the scattered ultrasonic waves received by a passive cavitation detector. By monitoring the scattered ultrasonic waves received by a passive cavitation detector, properties of the ultrasonic exposure may be modified to enhance stable cavitation and/or inertial cavitation. In response to monitoring stable cavitation and/or inertial cavitation, the source transducer 22 may be adjusted to provide a modified ultrasonic exposure by modifying the pressure amplitude, the duty cycle, and/or the duration of the ultrasonic exposure; additionally, in response to monitoring stable cavitation, the active interval duration and rest period duration may also be modified to allow inflow of the nucleating agent. For example, if the scattered ultrasonic waves received by the passive cavitation detector indicate continued bubble activity, the source transducer 22 remains on. In a further example, if the scattered ultrasonic waves received by the passive cavitation detector decrease or if cavitation is not detected, a rest period is initiated to allow the nucleating agent to flow into the targeted treatment zone. In one embodiment, when the scattered ultrasonic waves of the derivative frequency drop below about twice the background noise level in the passive cavitation detection system, a rest period is initiated. As discussed hereinabove, monitoring of the scattered ultrasonic waves may be performed by the digital computing device 100.

As discussed above, allowing further vesicles to flow along the vascular system to locations proximate to the targeted treatment zone during the rest period may increase overall efficiency of the method for increasing the concentration of the therapeutic drug in the targeted treatment zone and/or for increasing the depth of penetration of the therapeutic drug in the targeted treatment zone. The methods may further include, during the rest period, providing an active interrogation ultrasound pulse at a fundamental frequency. A scattered ultrasonic wave is detected by the detection transducer 24, where the scattered ultrasonic wave includes at least one of a subharmonic frequency, harmonics of the fundamental frequency, an ultraharmonic frequencies, a plurality of ultraharmonic frequencies indicative of stable cavitation, and/or an inharmonic frequency indicative of inertial cavitation. Detection of the scattered ultrasonic wave by the detection transducer 24 confirms that the vesicles are positioned proximate to the targeted treatment zone of the patient, thereby confirming to the system 10 that initiation of a subsequent active interval of ultrasonic exposure is due. The digital computing device 100 may monitor the scattered ultrasonic wave generated by the active interrogation ultrasound pulse to determine if initiation of an active interval of ultrasonic exposure is appropriate.

In one particular aspect of this embodiment, the targeted treatment zone comprises atheromatous plaques accumulated subendothelially by the patient and drug delivery across a biological membrane is enhanced substantially throughout the targeted treatment zone.

It will be appreciated that the system 10 and methods disclosed herein are useful in drug delivery across the biological membrane. Additionally, it will be appreciated that the system 10 and methods disclosed herein are useful in the treatment of cardiovascular diseases including but not limited to atherosclerosis. Moreover, it will be appreciated that ultrasound-mediated enhancement of stable cavitation and/or inertial cavitation increases drug delivery across the biological membrane substantially throughout the targeted treatment zone.

The following non-limiting example illustrates the methods and systems of the present invention.

EXAMPLES

Example 1: Effects of Stable Cavitation on Drug Delivery Across a Biological Membrane Cavitation Nucleation with Infusion of Contrast Agent in an Ex Vivo Mouse Model.

An approach for inducing cavitation using infusion of a contrast agent, targeted echogenic liposomes was tested experimentally ex vivo. Excised mouse aortae were mounted in a flow system. Through the flow system and the aortae, 0.5% bovine serum albuminin (BSA) in phosphate-buffered saline (Sigma-Aldrich, St. Louis, Mo., USA) was circulated at a flow rate of 3.4 mL/min with a stroke rate of 200 beats per minute to simulate circulation through the aortae. Some of the flow was diverted through a bypass around the aortae in order to control the pressure to which the vessel was exposed, such that the flow rate through the aortae themselves was about 2.6 mL/min.

Using an inline catheter, 1.5 mL of Rhodamine-labeled and anti-ICAM-1-targeted echogenic liposomes (Rh-ELIP) in 0.5% BSA were injected proximal to each artery with a catheter concentration of 3.33 mg lipid/mL and a catheter flow rate of 3 mL/min. The flow rate in the aorta during a 30 second ELIP bolus injection was 5.3 mL/min. Thus, the diluted arterial concentration of ELIP was 1.8 mg lipid/mL.

The ex vivo aortae mounted in a sample chamber was suspended in a tank filled with 37° C. purified and degassed water. The aortae were aligned at the natural focus of a 2.5 cm, 1-MHz single element unfocused ultrasound transducer (Panametrics, Waltham, Mass., USA) with a 10 mm 3-dB beam width and 6.0 cm depth of field. A prototype, broadband cylindrically focused hydrophone designed for passive cavitation detection (Sonic Concepts Inc., Woodinville, Wash., USA) was aligned 90° to the beam of the 1-MHz transducer so that the confocal region encompassed the aorta.

The stable and inertial cavitation thresholds for ELIP suspended in BSA flowing inside an ex vivo mouse aorta were measured. These thresholds were used to select an ultrasound pressure amplitude for the exposure of ex vivo mouse aortae to be treated with Rh-ELIP. A passive cavitation detection technique was used to determine the stable and inertial cavitation thresholds during insonation with the 1-MHz continuous wave (CW) ultrasound.

For the aortae that received ultrasound treatment, the transducer cable was connected to the amplifier when the Rh-ELIP bolus was visually confirmed to be exiting from the artery, and was left connected for 30 seconds. The aortae were insonified with 1-MHz CW ultrasound at peak-to-peak pressure of 0.49 MPa and the passive cavitation detector was used to verify the duration of the resulting stable cavitation. This sound pressure level was chosen to be above the threshold of stable cavitation and below the threshold of inertial cavitation in 0.5% BSA with ELIP flowing through a mouse aorta as measured by the prior experiments. After the aortae were exposed or sham exposed to ultrasound, flow of 0.5% BSA was allowed to continue through the aortae for 4 minutes following the passage of the Rh-ELIP to provide a wash. The aortae were removed, marked with India ink (Koh-I-Noor, Bloomsbury, N.J., USA) for orientation, sliced in cross section, snap-frozen in Tissue-Tek Optimal Cutting Temperature compound (Sakura Finetek, Torrance, Calif., USA) and stored at −80° C. The perivascular saline was collected and analyzed in a spectrometer (Shimadzu, Kyoto, Japan) for the presence of Rh-ELIP.

Cavitation Thresholds.

With non-ICAM-1-targeted ELIP delivered during steady flow at a concentration of 1.8 mg/mL of lipid through the artery, the stable cavitation threshold during insonation with 1-MHz CW ultrasound was 0.43±0.02 MPa peak-to-peak pressure amplitude, and the inertial cavitation threshold was 0.51±0.01 MPa. Based on these results, 1-MHz CW ultrasound can be applied to ex vivo aorta with ELIP to achieve stable cavitation or inertial cavitation at low peak-to-peak acoustic pressure amplitudes.

When aortae were exposed to a 0.49 MPa peak-to-peak pressure amplitude, passive cavitation signals from arteries treated with both Rh-ELIP and 1-MHz ultrasound displayed strong peaks at one half of the fundamental frequency as well as odd multiples of this subharmonic. No increase in broadband signal was present. This indicates that the aortae were exposed to stable cavitation, but not inertial cavitation. The stable cavitation signal persisted throughout the 30 second treatment period for each artery exposed to ultrasound.

Rh-ELIP Fluorescence Histology.

Figure 6:
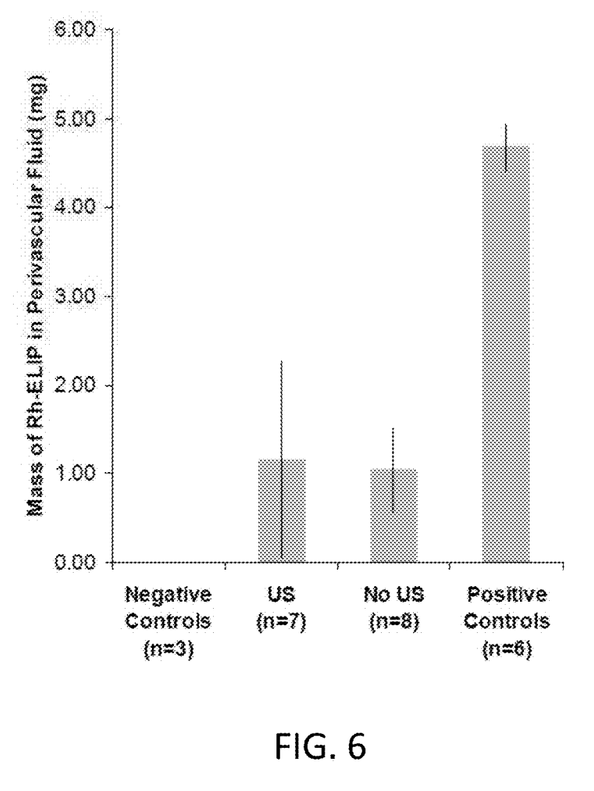
FIG. 6 is a graph depicting the mass of Rhodamine-labeled echogenic liposomes in ex vivo mouse aortae models according to one or more embodiments shown and described herein.

Enhanced fluorescence was observed on the endothelial cells of mouse aortae exposed to anti-ICAM targeted. As this fluorescence was qualitatively greater than the autofluorescence of arteries not exposed to Rh-ELIP, the endothelial enhancement was interpreted as successful targeting of Rh-ELIP to the endothelium. This enhancement was observed in six of seven arteries exposed to 1-MHz ultrasound, and in five of seven arteries not exposed to ultrasound, as depicted in FIG. 6. In some arteries, penetration beyond the endothelium was observed.

Analysis of Rh-ELIP Targeting and Ultrasound Treatment.

In 10 of 10 arteries exposed to intravascular Rh-ELIP in flowing BSA, Rhodamine-enhanced red-filtered fluorescence was observed on the endothelium. Sites of Rh-ELIP location corresponded well with sites of ICAM-1 expression on the endothelium. There were 16 arteries originally in the treatment groups, but two yielded histology deemed unreadable by the assessor blinded to experimental conditions. Additionally, analysis of slides produced by immunostaining with the endothelial cell marker Factor VIII-related antigen showed that four arteries had endothelia that were entirely absent. This occurred in two arteries that were exposed to ultrasound and two that were not, and was likely due to excessive handling while placing the arteries into the flow system. In prepared slides of the remaining arteries the endothelium appeared either intact or partially desquamated, with desquamated cells present in the arterial lumen. This desquamation was observed in both treated and control segments and was determined to be an artifact of tissue embedding by a pathologist also blinded to experimental conditions.

Figure 7:
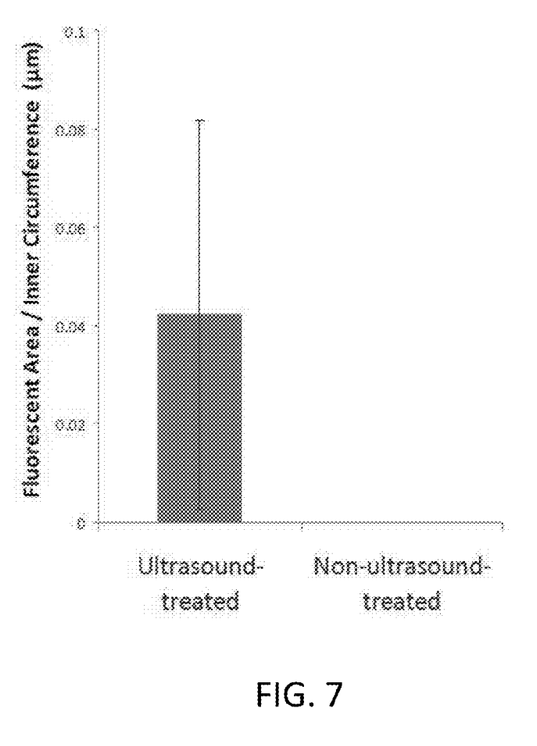
FIG. 7 a graph depicting ultrasound-induced penetration of Rhodamine-labeled echogenic liposomes in ex vivo mouse aortae models according to one or more embodiments shown and described herein.

It was hypothesized that ultrasound exposure of arteries during the Rh-ELIP bolus would result in enhanced penetration of the liposomes beyond the endothelial layer. In five of five arteries treated with ultrasound, penetration beyond the endothelium was observed, whereas none of the five arteries without ultrasound displayed sub-endothelial penetration. A quantitative assessment of the penetration of Rh-ELIP into the subendothelial tissues via image analysis of the histological slides of the aortae, is depicted in FIG. 7.

A one-tailed Wilcoxon-Mann-Whitney test showed that penetration of Rh-ELIP past the aortic endothelium is significantly greater in US-exposed arteries, with a p-value of 0.02. Rh-ELIP were never observed throughout the entire thickness of the arterial wall. The deepest red fluorescence was observed in an ultrasound-treated aorta at the fourth of six visible elastic lamellae in the tunica media, numbering from lumen to adventitia.

Example 2: Simulation of Sustained Cavitation in a Latex Tubing Model

To simulate measurement of sustained stable and/or inertial cavitation in a vascular system of a patient, stable cavitation and inertial cavitation was simulated in a latex tubing model. ELIP at a concentration of 0.02 mg/ml lipid in 0.5% BSA in PBS were pumped through a flow phantom consisting of 3.0 mm inner-diameter latex tubing at 5 ml/min using a peristaltic pump. ELIP were insonified in the tube using a 1 cm×1.5 cm color Doppler window from an L12-5 linear array on the Philips HDI-5000 scanner driven in duplex color Doppler mode. The Doppler pulses consisted of 10 cycles at a center frequency of 6 MHz with a PRF of 700 Hz, while the B-Mode frame rate was 12 Hz. Emissions from the insonified ELIP were recorded by a passive cavitation detector, or PCD (10-MHz, 2 cm focus, Valpey-Fisher, Hopkinton, Mass.), positioned orthogonal to the L12-5 array and flow tube and aligned with a color Doppler pulse located at the upstream edge of the color Doppler window. Acoustic emissions were recorded for each frame for 20 seconds.

because these signals contained acoustic scatter due to both the ELIP and the flow system, acoustic emissions not due to the ELIP were also recorded with filtered (0.2 μm), degassed (less than 60% $pO_2$), and deionized (18.0 MΩ2/cm) water flowing through the system and were subtracted to obtain the acoustic emissions from just ELIP. Data were collected at calibrated in situ peak rarefactional pressure amplitudes ($P_r$) of 0.07 to 1.76 MPa, which correspond to onscreen MI values of 0.04 to 0.90. Recorded emissions were processed in MATLAB (The Mathworks, Natick, Mass.). The power spectrum for the resulting signals was computed and averaged over the 20-s exposure duration. Correction for electronic noise in the ELIP power spectra at each pressure amplitude was achieved by subtracting the average noise energy in a high frequency band outside the array and PCD's bandwidth for each pressure amplitude setting. FIG. 5 depicts that for $P_r$>0.9 MPa (MI>0.45) it was possible to sustain cavitation for the first color Doppler pulse of each frame throughout the entire 20 s exposure period.

Both inertial cavitation (note the broadband elevation in the power spectrum with ELIP as compared to the spectrum with degassed water) and stable cavitation (note the peak at the subharmonic, 3-MHz and at the first ultraharmonic, 9-MHz) can be observed and their relative contributions adjusted by changing the insonation pressure.

It is noted that terms like "preferably," "generally," "commonly," and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A method for inducing and passively detecting stable cavitation for targeted drug delivery across a biological membrane, comprising:
   administering vesicles comprising a nucleating agent and a therapeutic drug to a target vascular system of a patient;
   providing intermittent active intervals of ultrasonic exposure substantially throughout a targeted treatment zone within the vascular system of the patient, said active intervals each lasting an active interval duration and being separated by rest periods, each rest period lasting a rest period duration during which no ultrasonic energy is provided, wherein the ultrasonic exposure is produced by a source transducer at a specified fundamental frequency, amplitude, duty cycle, and duration;
   detecting a scattered ultrasonic wave, wherein the scattered ultrasonic wave is received by a detection transducer and the scattered ultrasonic wave comprises a derivative frequency of the fundamental ultrasonic frequency comprising at least one of a subharmonic frequency and an ultraharmonic frequency, wherein detection of the derivative frequency is indicative of stable cavitation; and
   modifying the active interval duration and rest period duration to maintain stable cavitation by leaving the source transducer on when scattered ultrasonic waves of the derivative frequency are detected, and initiating a rest period when scattered ultrasonic waves of the derivative frequency decrease or are not detected.

2. The method for inducing and passively detecting stable cavitation of claim 1, wherein the method increases permeability of an endothelium of the patient to passage of the therapeutic drug across the endothelium.

3. The method for inducing and passively detecting stable cavitation of claim 1, wherein the source transducer and the detection transducer is selected from the group consisting of an annular transducer array, a linear transducer array, and a two-dimensional transducer array.

4. The method for inducing and passively detecting stable cavitation of claim 1, wherein the detection transducer comprises a passive cavitation detector selected from the group consisting of a hydrophone and a transducer array.

5. The method for inducing and passively detecting stable cavitation of claim 1, wherein the source transducer produces a fundamental ultrasonic frequency from about 100-kHz to about 15-MHz.

6. The method for inducing and passively detecting stable cavitation of claim 1, wherein the vesicles are echogenic liposomes.

7. The method for inducing and passively detecting stable cavitation of claim 1, further comprising monitoring the scattered ultrasonic waves received by the detection transducer and adjusting the pressure amplitude, duty cycle, duration of the ultrasonic exposure produced by the source transducer and duration of the rest period in order to maintain stable cavitation.

8. The method for inducing and passively detecting stable cavitation of claim 1, wherein the targeted treatment zone comprises atheromatous plaques accumulated subendothelially by the patient.

9. The method for inducing and passively detecting stable cavitation of claim 1, wherein the fundamental frequency, amplitude, duty cycle, and duration of the ultrasonic exposure is predetermined based on the excitation properties of the nucleating agent and the permeability of the biological membrane.

10. The method according to claim 1 wherein the rest period durations are between 100 milliseconds and 5 minutes and the active interval durations are between 10 milliseconds and five minutes.

11. The method according to claim 1 wherein the rest period durations are between 1 second and 60 seconds and the active interval durations are between 10 milliseconds and 10 seconds.

12. The method according to claim 1 wherein the rest period durations are between 1 second and 30 seconds.

13. The method according to claim 1 wherein the active interval durations are 8.5 seconds.

14. The method for inducing and passively detecting stable cavitation of claim 1 further comprising providing an active interrogation ultrasound pulse after the duration of one of the rest periods, wherein if the scattered ultrasonic wave comprising the derivative frequency is detected, then the vesicles comprising the nucleating agent and the therapeutic drug are positioned proximate to the targeted treatment zone of the patient and an active interval is resumed, and if the scattered ultrasonic wave comprising the derivative frequency is not detected, a rest period is re-initiated.

15. The method for inducing and passively detecting stable cavitation of claim 14, wherein the scattered ultrasonic wave includes a plurality of ultraharmonic frequencies of the fundamental ultrasonic frequency.

16. The method for inducing and passively detecting stable cavitation of claim 14, wherein the scattered ultrasonic wave includes a plurality of ultraharmonic frequencies of the fundamental ultrasonic frequency.

17. The method for inducing and passively detecting stable cavitation of claim 1, wherein the nucleating agent is selected from the group consisting of nanobubbles, microbubbles, and ultrasound contrast agents.

18. The method for inducing and passively detecting stable cavitation of claim 17, wherein the ultrasound contrast agent is perflutren-lipid microspheres.

* * * * *